United States Patent [19]

Johnson et al.

[11] Patent Number: 4,842,578
[45] Date of Patent: Jun. 27, 1989

[54] SURGICAL ABRADING INSTRUMENT

[75] Inventors: Lanny L. Johnson, Okemos, Mich.; Robert E. Brissette, Lynnfield, Mass.

[73] Assignee: Dyonics, Inc., Andover, Mass.

[21] Appl. No.: 186,645

[22] Filed: Apr. 14, 1988

Related U.S. Application Data

[63] Continuation of Ser. No. 840,462, Mar. 12, 1986, abandoned, which is a continuation of Ser. No. 587,554, Mar. 8, 1984, abandoned, which is a continuation-in-part of Ser. No. 237,895, Feb. 25, 1982, abandoned.

[51] Int. Cl.⁴ .............................................. A61B 17/32
[52] U.S. Cl. ..................................... 604/22; 128/305; 128/92 V
[58] Field of Search ................ 128/305, 305.1, 92 VJ, 128/92 V; 604/22; 433/125

[56] References Cited

U.S. PATENT DOCUMENTS

| 3,937,222 | 2/1976 | Banko | 128/305 |
| 3,976,077 | 8/1976 | Kerfoot | 128/305 |
| 4,203,444 | 5/1980 | Bonnell et al. | 128/305 X |
| 4,320,761 | 3/1982 | Haddad | 128/305 |
| 4,445,509 | 5/1984 | Auth | 128/305 |

FOREIGN PATENT DOCUMENTS

| 596229 | 3/1978 | U.S.S.R. | 128/305 |
| 623551 | 8/1978 | U.S.S.R. | 128/310 |
| 762870 | 9/1980 | U.S.S.R. | 128/305 |
| 2087239 | 5/1982 | United Kingdom | 128/305 |

Primary Examiner—Michael H. Thaler

[57] ABSTRACT

A surgical instrument includes the combination of a distally, side-supported inner drive shaft carrying on its end an abrading element, a fixed outer tubular member surrounding the inner shaft and providing at a bearing region the distal support for the inner shaft. A distal extension of the tubular supporting member provides a sheath for a portion of the abrading element and a vacuum passage communicating proximally from the region of the abrading element, past the bearing region, to a proximal vacuum connection, whereby during driving of the shaft and drawing of suction through the connection, particles dislodged by the driven, side-supported abrading element may be drawn past the bearing region and out of the instrument. In one embodiment the drive shaft is an inner hollow tube, a chuck member secured to the distal end of the hollow tube is adapted to removably grip and drive the abrading element, and an entry way, distal of the chuck member, provides for entry of particles into the inner hollow tube, the distal portion of the interior of the inner tube communicating with the vacuum connection. A method of arthroscopic surgery employing one embodiment of the instrument to enable self-repair of degenerated joint surfaces is also disclosed.

11 Claims, 4 Drawing Sheets

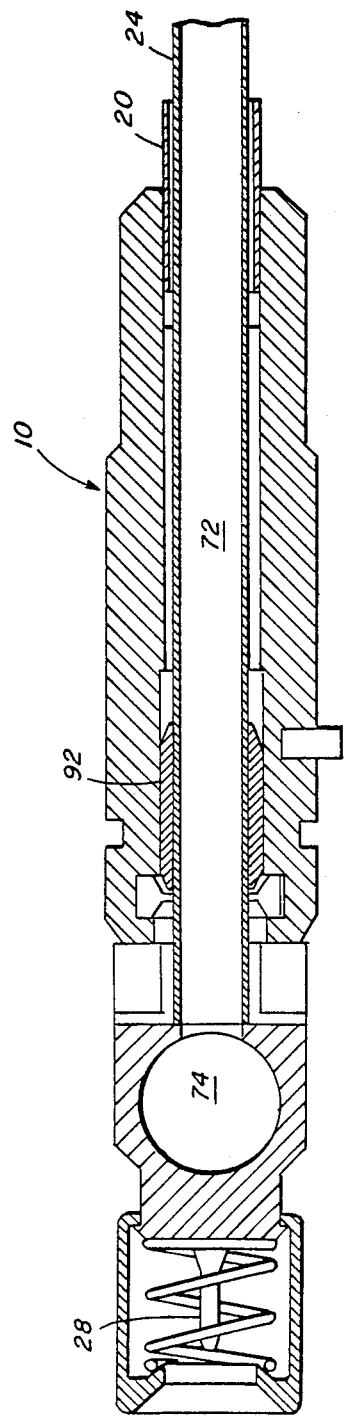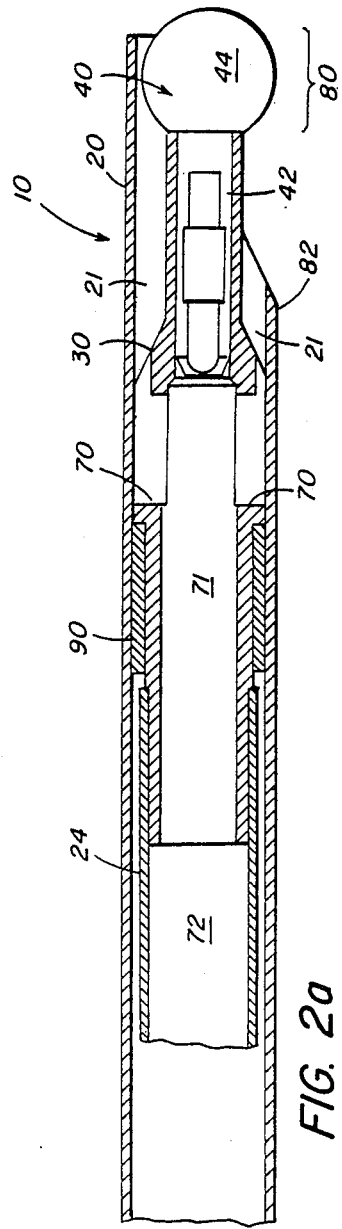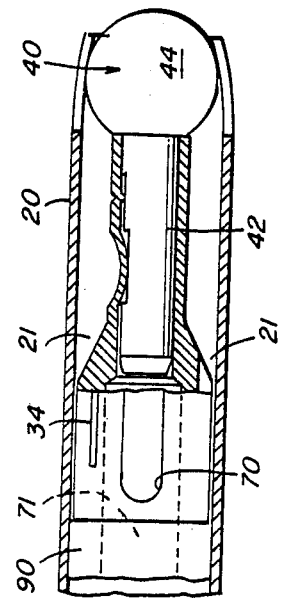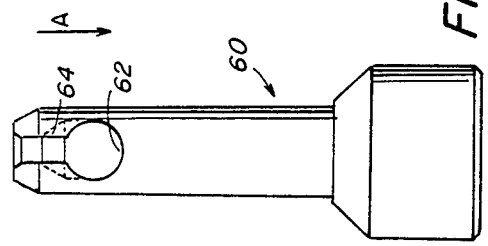

SURGICAL ABRADING INSTRUMENT

BACKGROUND OF THE INVENTION

This application is a continuation of application Ser. No. 84,462, filed Mar. 12, 1986, now abandoned; which is a continuation of application Ser. No. 587,554, filed Mar. 8, 1984, now abandoned; which is a continuation-in-part of U.S. Ser. No. 237,895, filed Feb. 25, 1982, and now abandoned.

The invention relates to surgical instruments, and in particular to instruments capable of use under remote visualization, e.g. within a joint via an arthroscope.

Although it was proven possible decades ago to visualize areas within the body of a human being by insertion of viewing probes, many surgical procedures, including surgery of the joints, have continued to be performed mainly by open surgery. Thus, in a typical joint operation, e.g. of the knee, hip, shoulder or elbow, although the object of the surgery for instance is to remove small amounts of tissue, e.g. cartilage or bone, a relatively large incision has been required. This takes a considerable time to heal which itself can cause trauma, discomfort and limitations of movement.

To anyone who might contemplate closed surgery of a space of the body, numerous restrictive and apparently conflicting requirements are encountered. For instance, the instrument should be small for maneuverability and ability to enter the region of interest and to limit trauma but large in order to transmit forces and to conduct away the matter to be removed; it should be safe from unwanted action against other surfaces, but capable of sufficiently strong action when desired. And above all, it should be reliable and capable of safe use by surgeons of varying skill.

Arthroscopic surgical instruments so-far developed, e.g. the Intra-articular Shaver corresponding to U.S. Pat. No. 4,203,444 by Bonnell et al., are highly effective for their intended purpose, but are not applicable to certain procedures such as those requiring removal of bone.

SUMMARY OF THE INVENTION

According to the invention, a surgical instrument comprises the combination of a distally, side-supported inner drive shaft carrying on its end an abrading element, a fixed outer tubular member surrounding the inner shaft and providing at a bearing region the distal support for the inner shaft, a distal extension of the tubular supporting member providing a sheath for a portion of the abrading element and a vacuum passage communicating proximally from the region of the abrading element, past the bearing region, to a proximal vacuum connection, whereby during driving of the shaft and drawing of suction through the connection, particles dislodged by the driven, side-supported abrading element may be drawn past the bearing region and out of the instrument.

In preferred embodiments, the drive shaft is an inner hollow tube, a chuck member secured to the distal end of the hollow tube is adapted to removably grip and drive the abrading element, and entry means, distal of the chuck member, provide for entry of particles into the inner hollow tube, the distal portion of the interior of the inner tube communicating with the vacuum connection, preferably the entry means is located distally of the bearing region; the tubular sheath and abrading element are sized to be inserted from the exterior through a puncture in the flesh of a living being and have sufficient length to extend to the situs of the surface upon which the abrading element is to act while the instrument is guided via visualization means; the instrument is adapted to be connected to an external vacuum source and is capable of removing fluid carrying abraded tissue from the region at a flow rate of the order of at least 100 cubic centimeters per minute; the shaft is adapted to be rotated at a speed of the order of at least 500 rpm under normal load; the drive shaft is adapted for rotation in forward and reverse direction under the control of the surgeon, and the abrading element is adapted to abrade less aggressively in the reverse direction than in the forward direction; and the distal portion of the tubular sheath is progressively relieved along one side to progressively expose the surface of the abrading element from one side, the distal end of the tubular sheath terminating proximally of the end surface of the abrading element, preferably the sheath is progressively relieved along a line which lies in a plane disposed at an angle of 30° or less to the axis of the tubular sheath.

According to another aspect of the invention, an arthroscopic method of surgery that enables self-repair of degenerated joint surfaces, comprises introducing into the joint from the outside the body via puncture wounds in the flesh: a conduit for introducing fluid, a visualization instrument, a rotary powered surgical abrading instrument, and means for removing fluid and severed tissue from the joint, introducing fluid through the conduit into the joint and actuating the means for removing fluid to establish a substantial volume of flow of fluid through the joint sufficient to remove severed joint tissue and to provide a clear field for viewing through the visualization instrument, positioning the visualization instrument to enable observation of the area of the joint surface to be surgically treated, on the basis of the visual observation, positioning the abrading element of the surgical instrument adjacent to the area of the joint surface, activating the abrading element of the surgical instrument, and progressively engaging the joint surface with the abrading element to uniformly remove a thin covering layer of articular cartilage and a thin layer of condylar bone to expose the underlying vascular bed while removing fluid and tissue severed by the abrading element by the removal means, whereby, after surgery, blood from the thus exposed vascular bed enables growth of a uniform layer of fibro cartilage over the joint surface.

In preferred embodiments of this aspect of the invention, the abrading element is shielded along one side, while another side and the end of the element are exposed for abrading action, preferably the surgical instrument includes the means for removing fluid and severed tissue, and the shield funnels the flow of fluid from the joint, by the abrading element, into the means to ensure effective removal of tissue abraded from the surface by the element; and the method includes removing the layer of bone to a depth of about 0.5 to 1.0 mm.

The instrument is found to have use in removing degenerated cartilage and bone of a load-bearing articular surface and exposing the profuse vascularity beneath the surface of the sclerotic bone over a selected area of the surface to enable fibrous growth and healing under the influence of this blood supplied by the vascular bed, thus to enable generation of fibro cartilage to cover the load bearing articular surface. The instrument also has other uses within the joint, e.g. the instrument can be effective for smoothing and shaping surface defects and irregularities, e.g. developed in the cartilage or formed during other procedures, to reduce the pain felt by the patient and improve the patient's joint mobility. The instrument has further use in percutaneous subdural procedures, e.g. for removal of underlying fat or scar tissue.

PREFERRED EMBODIMENT

The structure and operation of a preferred embodiment of the invention will now be described, after first briefly describing the drawings.

DRAWINGS

FIG. 2 is a longitudinal cross-sectional view partially broken away of the proximal end of the insrument of the preferred embodiment, FIG. 2a is a somewhat more enlarged view of the distal end, while FIG. 3 is a similar view of the extreme distal portion of the instrument turned 90°;

FIG. 4 is a longitudinal cross-sectional view of the instrument on an enlarged scale showing the chuck member, while

FIG. 7 is a similar view turned 9°, while

FIG. 9 is a side view of the tool for removing the abrading member of the invention;

Figure 4:
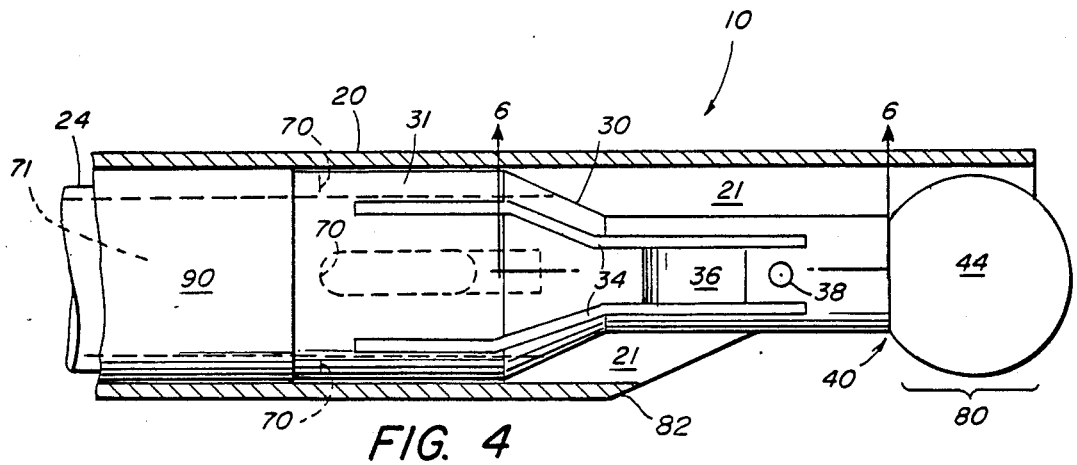
Figure 5:
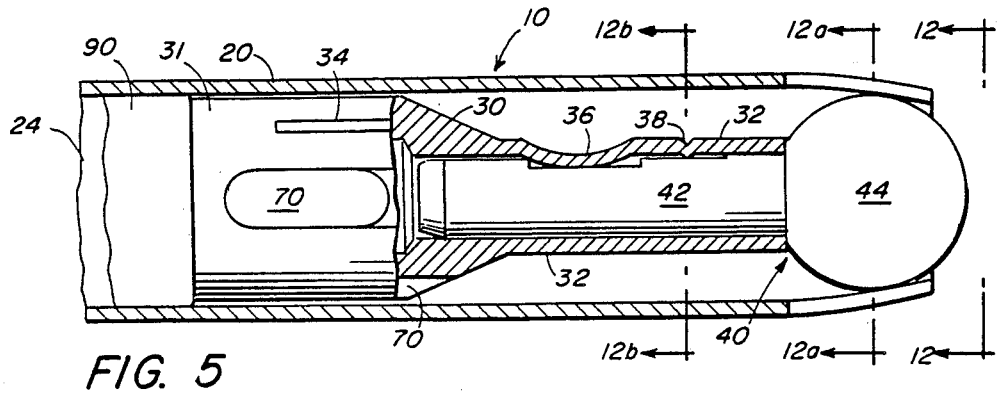
FIG. 5 is a similar view of the chuck member turned 90°.
Figures 12, 12A, 12B:
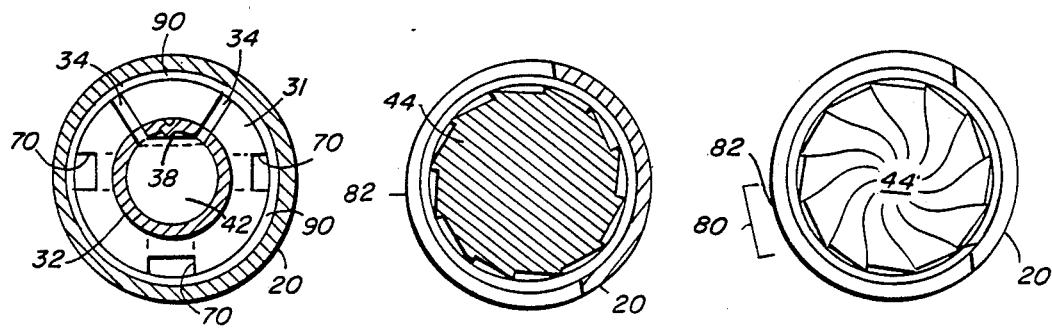

FIGS. 12, 12a, and 12b are end views of the top of the instrument taken at 12—12, 12a—12a, and 12b—12b of FIG. 4; and FIG. 13 is a longitudinal cross-sectional view partially broken away of the proximal end of an alternative embodiment of the invention, while FIG. 13a is an end sectional view taken at 13a—13a of FIG. 13.

Structure

Figure 1:
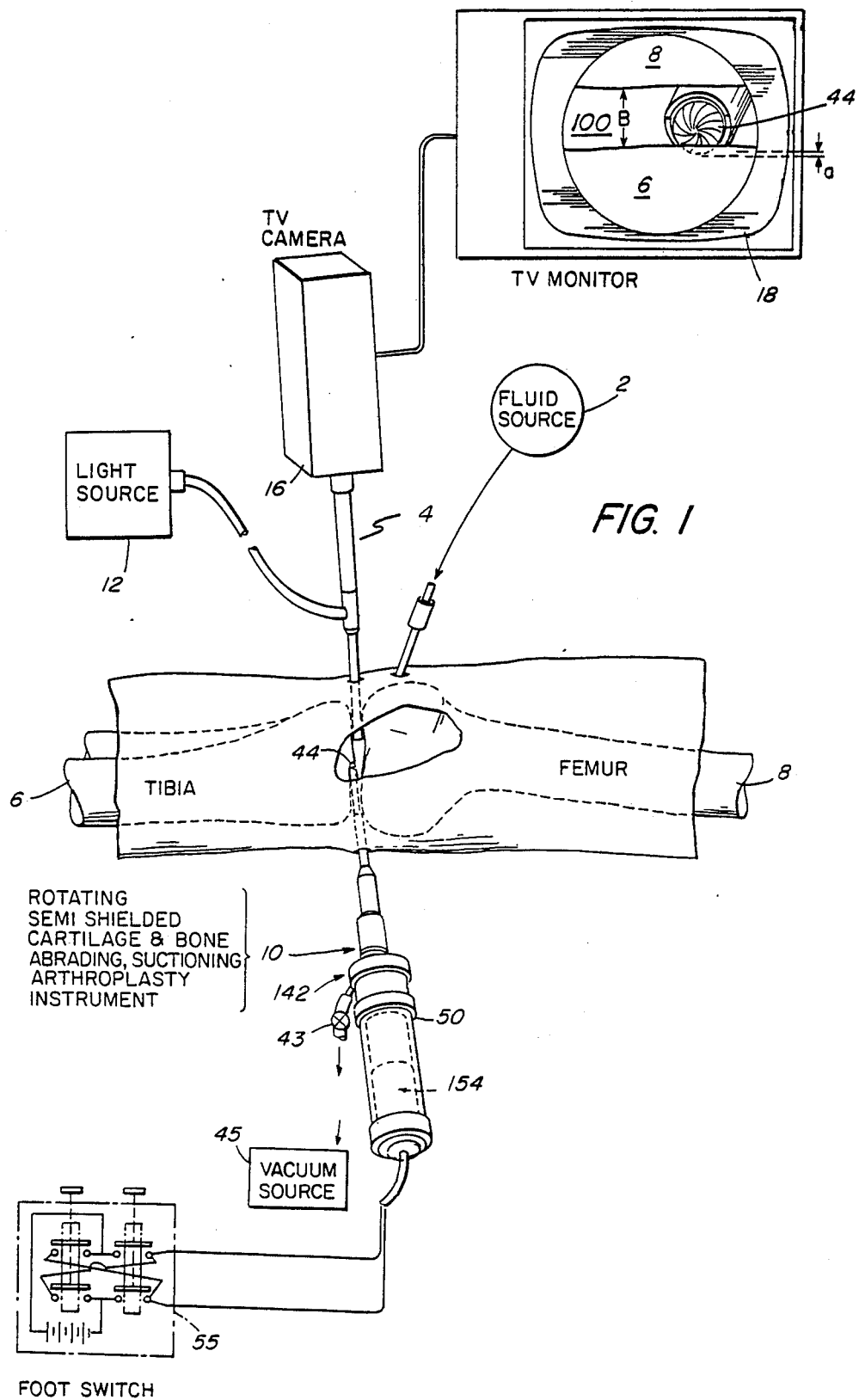
FIG. 1 is a diagrammatic view showing the set-up for performing arthroscopic surgery with the instrument according to the invention with accessories.
Figure 6:
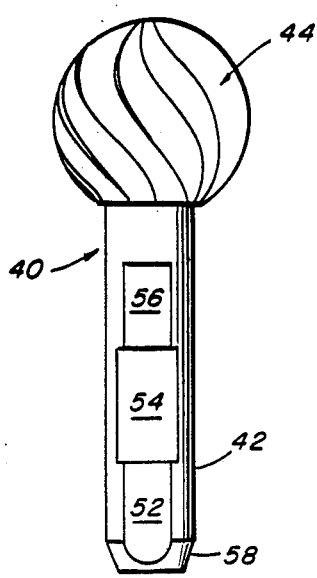
FIG. 6 is a side view of an abrading element according to the invention.
Figure 7:
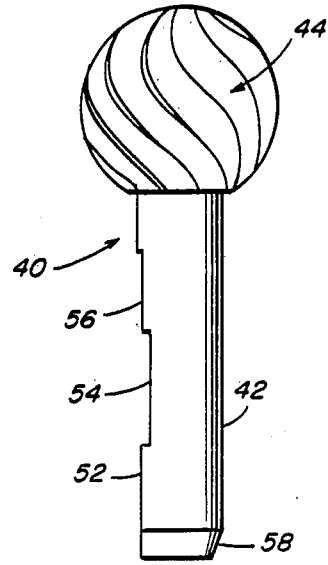
Figure 8:
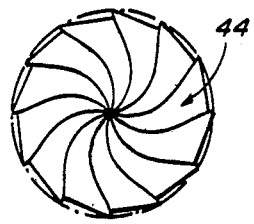
FIG. 8 is an end viewing showing the helical, fluted abrading surface of the element.
Figure 10:
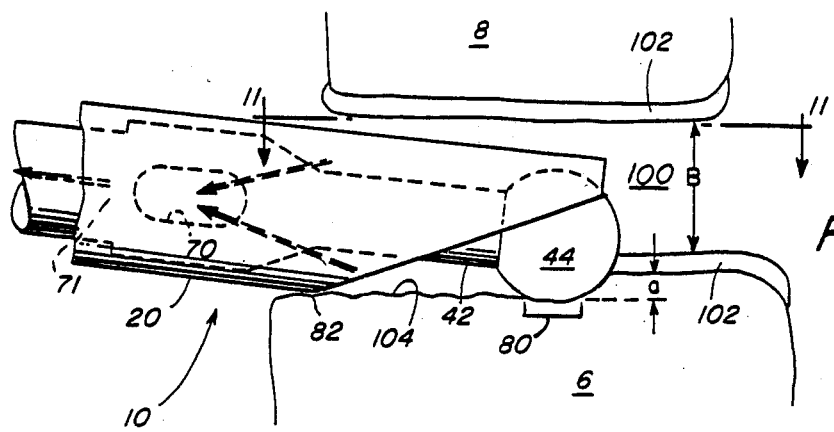
FIG. 10 is a diagrammatic view of the intra-articular surface of a joint undergoing arthroplasty of the vascular bed by an instrument according to the invention.
Figure 11:
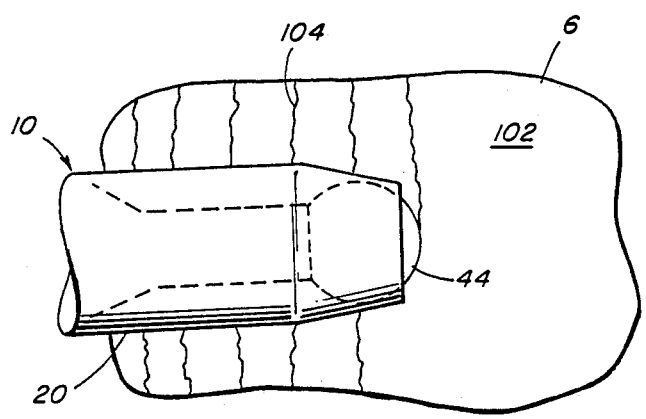
FIG. 11 is a top view at 11—11 of FIG. 10.

In FIGS. 1 and 2 the instrument 10 is shown inserted into a joint of the body. (A knee joint is shown by way of example, the instrument being inserted to act on the low friction load bearing condylar surfaces of the tibia 6 and the femur 8.) The joint is distended by providing a flow of saline fluid under controlled hydrostatic pressure from source 2. At the same time, a fiber optic visualization instrument 4 introduces light to the interior of the joint from light source 12 and returns a visual image along a separate optical path. While the image can be directed to an eye piece for the surgeon, as well as to recording cameras, in this embodiment, the image is directed to television camera 16 which recreates the display on screen 18. By watching the display screen and manipulating the instrument, the surgeon controls his movements and the instrument is caused to move across the joint, abrading the surface shown on the screen. (A more detailed view of surface appears in FIGS. 10 and 11, discussed below.)

The success of the instrument is dependent upon the important aspects of its construction as have been noted previously. Referring to FIGS. 2, 2a and 3, instrument 10 comprises an external tube 20 and an internal tube 24 inserted telescopically therein. For a typical instrument useful for surgery within the knee, the external tube 20 has an outer diameter of 7.5 mm and an inner diameter of 6.4 mm, and the internal tube 24 has an outer diameter of 5.2 mm and an inner diameter of 4.4 mm. (Instruments for use in smaller joints of the body, e.g. the shoulder, hip or elbow, or for smaller patients, may of course be smaller in diameter, e.g. the external tube having outer and inner diameters of 5.7 mm and 4.7 mm and the internal tube having outer and inner diameters of 4.2 mm and 3.8 mm. Instruments for percutaneous subdural surgery for removal of scar or fat tissue similarly have dimensions based on the intended use, the intended surgical site and the physical characteristics of the patient.)

The internal tube 24 is rotated relative to the external tube 20 by a drive train (FIG. 1), including a battery driven motor 54 in handle 50 acting on drive tang 28 (FIG. 2). The motor is reversible under the control of the surgeon, e.g. via a foot switch 55, and is adapted to produce torque values of the order of 2880 cm gms and to rotate the abrading element under normal bone-abrading load at speeds of the order of 500 up to about 3,000 rpm.

Referring to FIGS. 2a, 3, 4 and 5, fixed at the distal end of the internal tube is chuck 30, here a separately formed unit of heat treated stainless steel fixed axially on the internal tube 24 by use of an epoxy adhesive. The chuck 30 is formed to positively receive and hold the drive spur 42 of an abrading element 40 against the forces inherent during engagement of the instrument, e.g. on the surface of a joint. To meet this purpose, the wall 32 of the chuck 30 is cut axially at 34 and permanently deformed into a leaf-spring-like detent 36. The wall 32 is also deformed to provide an alignment guide 38. The abrading element 40 comprises rrive spur 42 and abrading head 44, with 12 helically fluted edges on its surface. For surgery in the knee joint, abrading head 44 may typically have a diameter of 5.5 mm, and drive spur 44 a diameter of 2.4 mm and a length of 10.3 mm. (In an instrument for use in smaller areas of the body, a head of smaller diameter, e.g. about 4.0 mm, may be employed.) The helical edges are so arranged that the abrading element cuts more aggressively in the forward than in the reverse direction of rotation. The head 44 and the spur 42 are machined from a single piece of heat treated stainless steel to reduce the potential of separation under the forces experienced during surgery, e.g. transverse displacement pressure of the order of 170 to 340 kg/cm$^2$. This abrading element is also disposable so a new sharp tool may be used for every procedure. The drive spur is provided with axial reliefs comprising alignment flat 52, detent flat 54 and clearance flat 56 for the alignment guide. The spur 42 also has an annular relief 58 at its proximal end to facilitate insertion of the spur into the chuck.

To prepare the instrument, the proximal end of drive spur 42 is inserted lightly into the distal end of chuck 30 and the abrading element 40 is rotated slowly until guide 38 is aligned with flat 52, signaled by the drive spur 42 moving proximally into the chuck 30. The abrading element 40 is urged proximally along its axis into the chuck until detent 36 is positioned upon detent flat 54, as indicated by the engagement of the shoulder of chuck 30 with the mating shoulder on abrading element 40. In this position, abrading head 44 is fixed on internal shaft 24 against the forces experienced during surgery.

To remove the abrading element 40, it is necessary to use the tool 60 shown in FIG. 9. (The inner tube 24 and the outer tube 20 are typically disassembled to facilitate this procedure.) Abrading head 44 and chuck 30 are passed through correspondingly shaped openings 62, 64 to engage head 44 in recess 63 with the chuck aligned coaxially with tool 60. Force is exerted along the axis as indicated by the arrow A to withdraw the drive spur 42 from the chuck. The abrading element may then be discarded and a new element inserted.

When assembled, the abrading head 44 extends axially beyond the distal end of the outer tube 20 by a distance of approximately one millimeter. (For knee surgery, the outer tube typically is at least 50 mm long.) The distal portion of outer tube 20 is also progressively relieved along one side at an angle to the axis of the tube, here at an angle of about 24°, shown in FIGS. 12 through 12b, to progressively expose the side surface 80 of the abrading head 44 at a position generally aligned with this external wall 82.

A major portion of the forces on the abrading element 44 are exerted from angles essentially perpendicular to the drive axis, thus it is necessary that the inner shaft 24 be supported against radial deflection, particularly under bone-abrading load. This support is provided by distal annular bearing 90, fixed to the external wall 31 of chuck 30 at a point where it will lie close to the distal end of outer tube 20 in the assembled instrument, and by proximal annular bearing 92, fixed on the wall of internal tube 24. Both bearings rotate with internal tube 24 supporting the tube against the interior wall of external tube 20. It is found that by providing the bearings as described, the frictional drag of the instrument is low, permitting the desired amount of torque (approximately 2880 cm gms) to be delivered to the abrading element. This torque is limited purposefully to avoid any unsafe overload condition.

Apertures 70 define suction ports through the wall of chuck 30 proximally of the drive spur detent 36 to provide a flow path out of the instrument via conduit 71 formed by the hollow chuck 30 through distal bearing 90 and conduit 72 formed by internal shaft 24 to permit removal of all the abraded tissue from the joint. The vacuum source 45 is external of the instrument, generally provided as "wall vacuum" in a surgicl suite, typically of a value of 14–16 in. Hg. The level of vacuum at the instrument is controlled by means of valve 43.

Operation of the Instrument

During an operative procedure, e.g. as shown in FIG. 1, the patient may be given general anesthesia and appropriate punctures of the patient's flesh are made at selected points about the joint by a trocarring cannula. Visualization instrument 4 is inserted into the joint through another cannula. The instrument 10, with the motor stopped, is inserted into the narrow cavity 100 (B being of the order of 8 mm) of the knee joint between the condylar surfaces of the tibia 6 and femur 8 to act on the thin layer 102 of cartilage and the below-lying condyl bone via a third cannula.

The fluid source 2 and the vacuum source 45 operating through the instrument 10 are balanced to provide uniform flow through the joint, with the inflow maintained at slightly higher pressure to appropriately distend the joint. The substantial volume of flow provided, e.g. in excess of 100 cc per minute in the knee, is necessary to ensure that all the material abraded from the joint is drawn into the instrument 10 and removed from the joint. It also keeps the joint fluid clear for better visual guidance of the instrument. The fluid is drawn across the abrading element into the annular cavity 21 between chuck 30 and the distal portion of external tube 20 and from there through suction port defining apertures 70 in the wall of chuck 30. Conduit 71 of chuck 30 carries the fluid through distal bearing 90 and into the conduit 72 formed by internal tube 24. Conduit 72 passes through proximal bearing 92 to discharge at sluff chamber 74 which, in turn, is connected within housing 42 to vacuum source 45. The relieved configuration of sluff chamber 74 allows suction to be continuously maintained during rotation of abrading element 40. The flow passages and operative parts of the instrument are thus cooperatively constructed for optimal action when the instrument is connected to the source of suction.

It has in the past been proposed, when the thin coating of articular cartilage that acts as a low-friction load bearing surface on the condylar surfaces of the tibia and femur degenerates, e.g., as is the case in degenerative arthritis, to drill at selected spaced apart points, into subchondral bone to a depth, e.g., of 3 or 4 mm, to expose the vascular bed with the hope of encouraging growth of fibro cartilage to regenerate an articular surface. In other instances curretage has been employed for the same purpose, but often with detrimental alteration of the surface contour.

It has, however, now been discovered that tiny, tissue-growth supporting blood vessels can be exposed by a shallow uniform abrasion of the joint surface using the instrument 10 which is particularly adapted to the purpose. Such a treatment can set the stage for uniform growth of cartilaginous tissue in a manner that can ease the arthritic pain and enable joint to work better, and, in certain cases, avoid total replacement of the knee, by relying upon the body's own ability to grow cartilaginous tissue on the articular surface. The instrument is especially well suited for implementation of this discovery, being of a size suitable for insertion from the exterior through a puncture in the flesh, and having sufficient length to extend into the joint to the situs of the joint surface, where it defines a shielded, bearing-supported, rotary-driven, bone abrading element, with suction communicating through the instrument to the bone abrading element.

The rotating semi-shielded cartilage and bone abrading head 44 of the suctioning instrument is moved across the surface of the joint to remove uniformly the thin covering layer of articular cartilage and a thin layer of bone (the subchondral bone is removed to a depth of about 0.5 to 1.0 mm) at the focus, i.e. the localized area of disease. This is done in a manner to provide a smooth surface 104, with the vascular bed generally exposed, which allows uniform generation of the fibro cartilage over the joint surface.

Other Embodiments

Other embodiments of the invention are within the following claims. For example, referring to FIGS. 13 and 13a, at the distal end of an instrument 10' of an alternate construction, abrading element 40 is inserted into chuck 30' at the distal end of internal tube 24'. The internal tube is rotatably supported by the external tube 20 via proximal annular support bearing 92' extending about internal tube 24' and by distal generally annular support bearing 90' extending about chuck 30'. As seen in FIG. 13a, distal support bearing 90' has generally longitudinally extending grooves 91' defined in the wall of bearing 90' between radially extending portions 93' which engage slidingly on the inner surface of the external tubing. Apertures 70' defined through the wall of internal tube 24' proximal to bearing 90' provide a flow path for fluid, abraded tissue and bone fragments from the region of operation of the abrading head 44, via grooves 91' in bearing 90', through apertures 70' into the inner volume of internal tube 24', which forms conduit 72 out of the body.

Oval or cylindrical or abrading elements of other shapes may be used according to the invention, and other abrading element surfaces, including a relatively smooth surfaces, may be employed. The dimensions provided are, of course, only by way of example and the sizes may be varied as desired.

What is claimed is:

1. A surgical instrument for a joint space of the body capable of performing intra-articular closed surgery through a puncture wound comprising the combination of an inner drive shaft carrying on its end a cartilage- and bone-abrading element, a fixed outer tubular member surrounding said inner shaft, said inner drive shaft carrying said abrading element and said surrounding outer tubular member sized and constructed for insertion into said joint space via said puncture wound, said outer tubular member providing, at a distal bearing region disposed only proximally of said abrading element, distal support for said inner shaft extending distally, in cantilever fashion, from said distal bearing region when subjected to side load during abrading of cartilage and bone by the side of said cartilage- and bone-abrading element,
   a distal extension of said tubular supporting member providing a sheath for a portion of said cartilage- and bone-abrading element sized and shaped to protect adjacent cartilage and bone surfaces of said joint and a vacuum passage communicating proximally from the region of said abrading element, past said bearing region, to a proximal vacuum connection, whereby during driving of said shaft and drawing of suction through said connection, cartilage and bone particles dislodged by the driven, side-supported cartilage- and bone-abrading element may be drawn past said bearing region and out of said instrument.

2. The surgical instrument for a joint space of the body of claim 1 wherein said inner drive shaft is an inner hollow tube, and entry means, distal of said distal bearing region, provide for entry of cartilage and bone particles into said inner hollow tube, the distal portion of the interior of said inner hollow tube communicating with said vacuum connection.

3. The surgical instrument for a joint space of the body of claim 1 or 2 wherein a chuck member secured to the distal end of said inner hollow tube is adapted to removably grip and drive said cartilage- and bone-abrading element.

4. The surgical instrument for a joint space of the body of claim 1 wherein said tubular sheath and cartilage- and bone-abrading element are sized to be inserted from the exterior through a puncture in the flesh of a living being and have sufficient length to extend to the situs of a cartilage or bone surface in said joint upon which said cartilage- and bone-abrading element is to act while the instrument is guided via an arthroscopic visualization means.

5. The surgical instrument for a joint space of the body of claim 1 wherein said instrument is adapted to be connected to an external vacuum source and is capable of removing fluid carrying cartilage and bone abraded tissue from said region at a flow rate of the order of at least 100 cubic centimeters per minute.

6. The surgical instrument for a joint space of the body of claim 1 wherein said drive shaft is adapted for rotation in forward and reverse direction under the control of the surgeon, and said cartilage- and bone-abrading element is adapted to abrade less agressively in the reverse direction than in the forward direction.

7. The surgical instrument for a joint space of the body of claim 1 wherein the distal portion of said tubular sheath is progressively relieved along one side to progressively expose the surface of said cartilage- and bone-abrading element from one side, the distal end of said tubular sheath terminating proximally of the end surface of said abrading element.

8. The surgical instrument for a joint space of the body of claim 7 wherein said sheath is progressively relieved along a line which lies in a plane disposed at an angle of 30° or less to the axis of said tubular sheath.

9. An arthroscopic method of surgery that enables self-repair of degenerated joint surfaces, comprising
   introducing into the joint from the outside the body via puncture wounds in the flesh:
      a conduit for introducing fluid,
      a visualization instrument,
      a rotary powered surgical abrading instrument comprising the combination of an inner drive shaft carrying on its end a cartilage- and bone-abrading element, a fixed outer tubular member surrounding said inner shaft, said inner drive shaft carrying said abrading element and said surrounding outer tubular member sized and constructed for insertion into said joint space via said puncture wound, said outer tubular member providing, at a distal bearing region disposed only proximally of said abrading element, distal support for said inner shaft extending distally, in cantilever fashion, from said distal bearing region when subjected to side load during abrading of cartilage and bone by the side of said cartilage- and bone-abrading element, a distal extension of said tubular supporting member providing a sheath for a portion of said cartilage- and bone-abrading element sized and shaped to protect adjacent cartilage and bone surfaces of said joint, and
      means for removing fluid and severed tissue from said joint,
   introducing fluid through said conduit into said joint and actuating said means for removing fluid to establish a substantial volume of flow of fluid through said joint sufficient to remove severed joint tissue and to provide a clear field for viewing through said visualization instrument,
   positioning the visualization instrument to enable observation of the area of the joint surface to be surgically treated,
   on the basis of said visual observation, positioning the abrading element of said surgical instrument adjacent to said area of the joint surface, activating the abrading element of said surgical instrument, and progressively engaging the joint surface with said abrading element to uniformly remove a thin covering layer of articular cartilage and a thin layer of condylar bone to expose the underlying vascular bed while removing fluid and tissue severed by said abrading element by the removal means, whereby, after surgery, blood from the thus exposed vascular bed enables growth of a uniform layer of fibro cartilage over the joint surface.

10. The method of claim 9 wherein said abrading element is shielded by said sheath along one side, while another side and the end of the element are exposed for abrading action.

11. The method of claim 10 wherein said surgical instrument includes said means for removing fluid and severed tissue, and said shield funnels the flow of fluid from the joint, about the abrading element, into said means, to ensure effective removal of tissue abraded from the surface by said element.

* * * * *

UNITED STATES PATENT AND TRADEMARK OFFICE
CERTIFICATE OF CORRECTION

PATENT NO. : 4,842,578

DATED : June 27, 1989

INVENTOR(S) : Lanny L. Johnson, et al

It is certified that error appears in the above-identified patent and that said Letters Patent is hereby corrected as shown below:

Title page, item [75], add--; Leonard J. Bonnell, Huntingdon Valley, Penn.-- as an inventor after "Robert E. Brissette, Lynnfield, Mass."

In the Abstract, line 18, replace "provides" with --provide--.

Column 1, line 6, replace "No. 84,462" with --No. 840,462--.

Column 2, line 26, delete "the" before "outside".

Column 3, line 20, replace "insrument" with --instrument--.

Column 3, line 30, replace "9°" with --90°--.

Column 3, line 65, insert --the-- before "surface".

Column 4, line 38, replace "rrive" with --drive--.

Column 6, line 36, insert --the-- before "joint".

Column 8, line 26, delete "the" before "outside".

Signed and Sealed this

Fifth Day of June, 1990

*Attest:*

HARRY F. MANBECK, JR.

*Attesting Officer*  *Commissioner of Patents and Trademarks*